United States Patent [19]

Frey et al.

[11] Patent Number: 4,745,914

[45] Date of Patent: May 24, 1988

[54] MEDULLARY CAVITY BARRIER

[75] Inventors: Otto Frey, Winterthur; Rudolf Koch, Berlingen, both of Switzerland

[73] Assignees: Sulzer Brothers Ltd., Winterthur; Protek AG, Berne, both of Switzerland

[21] Appl. No.: 903,553

[22] Filed: Sep. 3, 1986

[30] Foreign Application Priority Data

Oct. 10, 1985 [CH] Switzerland .................. 4373/85

[51] Int. Cl.[4] ............................................. A61F 2/28
[52] U.S. Cl. .................................. 128/92 VP; 623/16
[58] Field of Search ............... 623/16, 66; 128/92 VP, 128/92 R, 92 Y, 92 V, 1 R; 129/92 VQ

[56] References Cited

U.S. PATENT DOCUMENTS

| 4,425,908 | 1/1984 | Simon | 128/1 R |
| 4,447,915 | 5/1984 | Weber | 128/92 VP |
| 4,494,531 | 1/1985 | Gianturco | 128/1 R |

FOREIGN PATENT DOCUMENTS

| 0058744 | 9/1982 | European Pat. Off. | 623/16 A |
| 83/00011 | 1/1983 | PCT Int'l Appl. | 623/16 A |
| 2052267 | 1/1981 | United Kingdom | 623/16 A |

*Primary Examiner*—Richard J. Apley
*Assistant Examiner*—Alan W. Cannon
*Attorney, Agent, or Firm*—Kenyon & Kenyon

[57] ABSTRACT

The medullary cavity barrier is made of a metal in a rosette manner with leaves which are permanently and elastically deformable. The barrier is porous to the extent of being permeable to blood, fat and gases but impermeable to the passage of bone cement. During implantation, each outwardly extending leaf bends relative to a central core to fix the barrier within a tubular bone.

10 Claims, 1 Drawing Sheet

MEDULLARY CAVITY BARRIER

This invention relates to a medullary cavity barrier for insertion in a tubular bone.

As is known, medullary cavity barriers or plugs have been used to prevent bone cement from penetrating into the medullary cavity of a tubular bone which is contiguous to a surgically prepared cutout for the insertion of a prosthesis shank. Generally, for bones which become narrower in the direction of insertion, the medullary cavity barriers consist of a stopper-like cylindrical or conical core such as described in European Patent Application No. 0023787. In addition, these barriers have also been fitted with lobe-like leaves (petals) possibly in one or more garlands, such as described in European Patent Application No. 0006408, U.S. Pat. No. 4,293,962 and British Patent No. 2,017,503. In this latter case, the leaves have been elastically deformable and enclose, at least in a deformed state, in the manner of a calyx, a cavity which is open toward the surgical opening. Further, the core and leaves have been made of plastic.

However, if the end of a surgical cutout is disposed in a bone which widens in the direction of insertion, the above constructions are unsuitable since the barriers cannot be fixed at a defined level with any necessary certainty. For such cases, an expandable medullary cavity barrier has been used. In this case, the barrier has been formed of an elastically deformable outer body and an expansion element which is introduced into the outer body from the side away from the surgical cutout. When inserted, the expansion element expands the outer body and fixes the outer body in the bone cavity and itself becomes dovetailed with the outer body to become thus retained. Such a construction is described in European Patent No. 0058744. In this case, the barrier has also been made of plastic. However, the construction is costly and the technique of inserting the barrier has been complicated.

Although a number of the above types of constructions have been provided with through-bores, each involves a problem in that, as the bone cement is being introduced, blood and adipose tissue, which collect in the surgical cutout near the base, are not sufficiently expelled from the cavity which is to be filled with the cement. Thus, inclusions of blood and adipose tissue and/or air will form in the bone cement bed leading to a loss of strength of the cement bed.

Accordingly, it is an object of the invention to provide a simple and easy to handle medullary cavity barrier which can be inserted in a narrowing as well as in a widening bone cavity and which can be fixed therein and which has a relatively great permeability for blood, adipose tissue and gases.

It is another object of the invention to provide a relatively simple low cost medullary cavity barrier which can be inserted in a tubular bone in a relatively simple manner.

It is another object of the invention to provide a medullary cavity barrier which is permeable to blood and fat and impermeable to bone cement.

Briefly, the invention provides a medullary cavity barrier for insertion in a tubular bone which is comprised of a one piece body having a rosette shape with at least three radially extending leaves, each of which is elastically and permanently deformable. In addition, the body is made of a metal which is permeable to blood and fat while being impermeable to bone cement.

The high plastic and elastic deformability of metals permits an approximate adaptation of the barrier to a surgically prepared cavity or cutout with the aid of plastic deformation. At the same time, the degree of additional elastic deformation that determines fixation is also adjusted. The types of metals used for the barrier include those metals particularly, titanium or titanium alloys.

In order to enhance the porosity of the barrier, the one piece body is made of a metal wire mesh, or of any suitable reticular structure, or the use of perforated sheets. The porosity is such that the barrier is permeable for gases and for liquids of low viscosity, such as blood, while pasty bone cement cannot penetrate through the barrier. In use, after implantation of the barrier, as a bone cement is being filled in, gas, blood, fat and secretions are driven out of the surgical cavity so that there will be no inclusions in the polymerizing bone cement that would lead to a weakening of the cement bed. When made of wire mesh, the barrier may be composed of several layers if necessary, for example, for reasons of strength In order to provide good fixation by means of an elastic clamping, it has proven appropriate if the leaves of the rosette are bent at an angle out of the basic plane. To this end, the barrier includes a central core with each leaf extending from the core in a common plane to a first bend and, therefrom, at an angle to the common plane such that the leaves define a calyx. In order to protect the surrounding bone from damage, the free ends of the leaves are bent toward the center of the rosette, that is, radially inwardly.

These and other objects and advantages of the invention will become more apparent from the following detailed description taken in conjunction with the accompanying drawings wherein.

Figure 1:
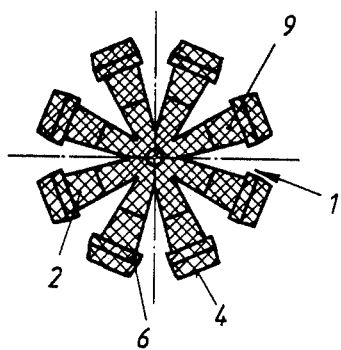
FIG. 1 illustrates a plan view of a medullary cavity barrier constructed in accordance with the invention.

Referring to FIG. 1, the medullary cavity barrier is formed of a one piece body 1 having a rosette shape including a central core from which eight leaves 2 extend radially outwardly. The one piece body is produced from a wire mesh of titanium or a titanium alloy, for example, by stamping. Further, each leaf 2 has a width which increases continuously from the core outwardly. Initially, when stamped, the leaves 2 are flat. However, after stamping, each leaf 2 is permanently deformed at two bends 3, 4 in order to form a calyx as shown in FIG. 2.

Figure 2:
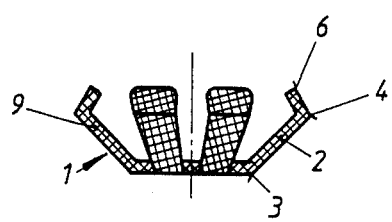
FIG. 2 illustrates a side view of the barrier of FIG. 1.

Referring to FIG. 2, each leaf 2 extends from the central core in a common plane to the first bend 3 and thereafter extends at an angle to the common plane to the bend 4. Each leaf 2 then extends radially inwardly to a free edge 6.

The body of the barrier is chacterized as being permeable to blood and fat while being impermeable to bone cement. This characteristic can be obtained by virtue of the wire mesh construction of the barrier. For purposes of strength, the wire mesh may be of multilayer construction. In any event, the wire mesh is formed with openings 9 through which the permeable materials are to flow.

Figure 3:
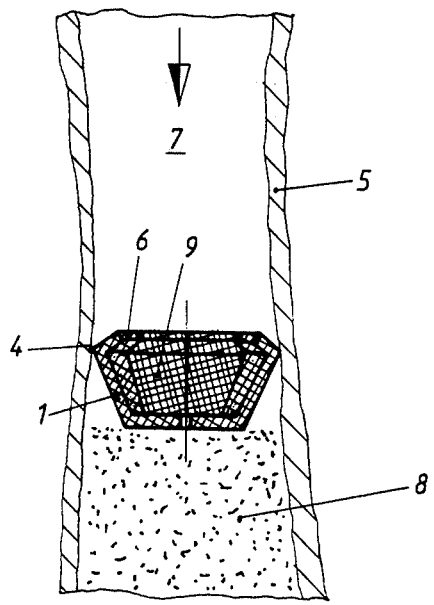
FIG. 3 illustrates a longitudinal sectional view through a bone cavity which expands inwardly and in which a medullary cavity barrier has been inserted in accordance with the invention.

Referring to FIG. 3, the medullary cavity barrier which has been preformed as indicated in FIG. 2 is inserted into a tubular bone 5 from above, as viewed. In this regard, the bone 5 has been surgically prepared to define a cavity 7. Thereafter, the leaves are permanently deformed to be nearly adjusted to the cross-section of the cavity and the cavity barrier is inserted into the cavity 7. During insertion, the leaves 2 undergo an additional elastic deformation along their lengths and at the bends 3. With at least a partial 'releasing' of the elastic deformations and with the bends 4 engaging the side walls of the bone 5, a suitable fixation of the barrier is achieved within the bone 5 by clamping. Of note, the bends 4 have the function of protecting the bone 5 from damage by the free edges 6, although rounded, as the barrier is being inserted.

After insertion in the bone 5, the cavity barrier forms a "macroscopically" closed barrier for the passage of bone cement from the surgical opening 7 into the "undamaged" bone filled with marrow and spongiosa 8. At the same time, the barrier 1, having a porosity which is permeable to blood, fat and gases, functions as a separating wall between the bone cement and the body fluids and tissues so that the cement is not contaminated and thus weakened in strength.

The invention thus provides a medullary cavity barrier of relatively simple construction and one which can be readily manufactured and handled. Further, the invention provides a medullary cavity barrier which can be easily manipulated by a surgeon into a surgically prepared bone cavity in a relatively simple and efficient manner.

Still further, the invention provides a medullary cavity barrier which is able to permit passage of blood and fat while being impermeable to bone cement so as to preclude inclusion of the blood and fat into the hardening bone cement bed.

What is claimed is:

1. A medullary cavity barrier for insertion in a tubular bone, said barrier comprising a one piece metal body having a rosette shape with at least three radially extending leaves, each said leaf being elastically and permanently deformable, said body being permeable to blood and fat and impermeable to bone cement.

2. A medullary cavity barrier as set forth in claim 1 wherein said body is made of a metal wire mesh.

3. A medullary cavity barrier as set forth in claim 2 wherein said body is of multi-layer construction.

4. A medullary cavity barrier as set forth in claim 1 wherein said body includes a central core and each leaf extends from said core in a common plane to a first bend and extends from said first bend at an angle to said plane whereby said leaves define a calyx.

5. A medullary cavity barrier as set forth in claim 4 wherein each leaf extends from said first bend to a second bend to extend radially inwardly.

6. A medullary cavity barrier as set forth in claim 1 wherein each leaf is of increasing width from said core outwardly.

7. A medullary cavity barrier for insertion in a tubular bone, said barrier comprising a porous one piece metal body having a rosette shape with at least three radially extending leaves, each said leaf being elastically and permanently deformable and said body having a porosity which is permeable to blood and fat and impermeable to bone cement.

8. A medullary cavity barrier as set forth in claim 7 wherein said body is made of a metal wire mesh.

9. A medullary cavity barrier as set forth in claim 7 wherein said body includes a central core and each leaf extends from said core in a common plane to a first bend and extends at an angle from said first bend to a second bend to extend radially inwardly.

10. A medullary cavity barrier as set forth in claim 9 wherein each leaf is of increasing width from said core outwardly.

* * * * *

UNITED STATES PATENT AND TRADEMARK OFFICE
CERTIFICATE OF CORRECTION

PATENT NO.   : 4,745,914

DATED        : May 24, 1988

INVENTOR(S)  : Otto Frey, et al

It is certified that error appears in the above-identified patent and that said Letters Patent is hereby corrected as shown below:

Column 2, line 9 "metals particularly" should be -metals and metal alloys which are common in implant technology particularly- Signed and Sealed this First Day of November, 1988

Attest:

Attesting Officer

DONALD J. QUIGG

Commissioner of Patents and Trademarks